(12) United States Patent
Pan et al.

(10) Patent No.: US 9,153,208 B2
(45) Date of Patent: *Oct. 6, 2015

(54) SYSTEMS AND METHODS FOR IMAGE DATA MANAGEMENT

(71) Applicant: Nephosity, Inc., San Francisco, CA (US)

(72) Inventors: Michael Pan, Arcadia, CA (US); Zehao Chang, Hong Kong (HK); John Pan, Brookline, MA (US)

(73) Assignee: NEPHOSITY, LLC, Powell, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/284,953

(22) Filed: May 22, 2014

(65) Prior Publication Data

US 2014/0253587 A1 Sep. 11, 2014

Related U.S. Application Data

(63) Continuation of application No. 13/354,627, filed on Jan. 20, 2012, now Pat. No. 8,773,463.

(51) Int. Cl.
*G09G 5/36* (2006.01)
*G06F 19/00* (2011.01)

(52) U.S. Cl.
CPC ............... *G09G 5/36* (2013.01); *G06F 19/321* (2013.01); *G09G 2340/04* (2013.01); *G09G 2340/0407* (2013.01); *G09G 2370/022* (2013.01); *G09G 2380/08* (2013.01)

(58) Field of Classification Search
None
See application file for complete search history.

(56) References Cited

U.S. PATENT DOCUMENTS

| | | | |
|---|---|---|---|
| 7,529,420 | B2 | 5/2009 | Li |
| 2008/0273787 | A1 | 11/2008 | Ducksbury et al. |
| 2009/0262121 | A1 | 10/2009 | Opala et al. |
| 2011/0019911 | A1 | 1/2011 | Yamazaki |
| 2013/0162678 | A1 | 6/2013 | Harris |

*Primary Examiner* — Maurice L McDowell, Jr.
(74) *Attorney, Agent, or Firm* — Cotman IP Law Group, PLC

(57) ABSTRACT

A system and method for image data management. A tiled representation of a data set is accessed. The tiled representation includes a plurality of high-resolution tiles and a plurality of reduced-resolution tiles. A request to access said data set from a computing device is received. An image display window is determined based on said request from the computing device, where the image display window corresponds to a displayable image for display on the display device. At least one overlapping image to send the computing device is determined based on said image display window, where the at least one overlapping image is selected from the scaled full images, the plurality of high-resolution tiles, and the plurality of reduced resolution tiles. At least a portion of the at least one overlapping image is sent to the computing device.

20 Claims, 13 Drawing Sheets

SYSTEMS AND METHODS FOR IMAGE DATA MANAGEMENT

CROSS REFERENCE TO RELATED APPLICATIONS

The present application is a continuation of U.S. patent application Ser. No. 13/354,627, filed on Jan. 20, 2012, specification of which is herein incorporated by reference in its entirety.

BACKGROUND OF THE INVENTION

1. Field of the Invention

Embodiments of the invention described herein pertain to the field of computer systems. More particularly, but not by way of limitation, one or more embodiments of the invention enable systems and methods for image data management.

2. Description of the Related Art

Access to high-resolution image data is useful in a wide variety of applications. In almost any field, high-resolution image data is desirable over lower resolution images. Image size and/or image resolution are often reduced to provide quicker access or to facilitate access to mobile devices with limited resources. Often, high-resolution image data can enhance user experience.

In some applications, access to high-resolution image data is necessary. For example, although providing quick access to lower resolution medical imaging data may be useful, full resolution medical imaging data must be consulted before making a final diagnosis. Other important high-resolution image data that may also be important include mapping, schematics, geographical data, advertising, publishing, design, professional photography, and other types of image data.

Often, high-resolution image data involves private, confidential or sensitive information that cannot be made publicly available for download. In these instances, it is standard to store high-resolution image data on a secure, centralized server. Access to the high-resolution image data may be granted to authorized users through standard security protocols.

It is desirable to provide high-resolution image data to computing devices, even when the computing devices have limited computing resources. Limited computing resources may include processing power, graphical processing power, memory, network bandwidth, and any other computing resource. At the same time, there is a demand for access to high-resolution image data at near real-time speed. In one instance, the resolution of the file may be reduced to provide quicker access at the expense of image resolution. In another instance, the high-resolution image data file may be downloaded before a user may view and navigate the image file. However, the delay involved in downloading larger image data files makes this method less useful, especially if collaboration is desired.

In a typical collaboration scenario, one specialist may seek the advice or opinion of another specialist regarding the high-resolution image data. However, existing solutions do not providing the second specialist quick access to the high-resolution image data at near real-time speed.

To overcome the problems and limitations described above, there is a need for systems and methods for image data management.

BRIEF SUMMARY OF THE INVENTION

Systems and methods for image data management described herein provide high-resolution image data at near real-time speed by preprocessing the high-resolution image files into tiles of varying resolution. A client device requests image data based on user navigation within the image file. Depending on an image display window, a subset of tiles at the desired resolution is sent to the client device, resulting in access to the high-resolution image data at near real-time speed.

One or more embodiments of the system and method for image data management described herein enable a computer-readable medium including computer-readable instructions for providing image data. Execution of the computer-readable instructions by one or more processors causes the one or more processors to carry out steps.

One of the steps carried out by the one or more processors is accessing a tiled representation of a data set including image data at high-resolution. The tiled representation may include a plurality of high-resolution tiles, where none of the plurality of high resolution tiles is larger than a maximum tile size. The tiled representation may further include a plurality of reduced-resolution tiles, where none of the plurality of reduced resolution tiles is larger than the maximum tile size.

Another step carried out by the one or more processors is receiving a request to access the data set from a computing device. The computing device is communicatively coupled with a display device.

Another step carried out by the one or more processors is determining an image display window based on the request from the computing device. The image display window corresponds to a displayable image for display on the display device.

Another step carried out by the one or more processors is determining at least one overlapping image to send the computing device based on the image display window. The at least one overlapping image is selected from the plurality of high-resolution tiles and the plurality of reduced resolution tiles.

Another step carried out by the one or more processors is sending at least a portion of the at least one overlapping image to the computing device for display in real time.

In one or more embodiments, the steps may further include obtaining a data set including image data at high-resolution, generating a plurality of scaled full images at a plurality of resolutions that includes a full resolution image and at least one reduced resolution image, generating a plurality of high-resolution tiles based on the full resolution image, where none of the plurality of high resolution tiles is larger than a maximum tile size, and generating a plurality of reduced-resolution tiles based on the at least one reduced resolution image, where none of the plurality of reduced resolution tiles is larger than the maximum tile size; and storing the tiled representation of the data set.

For example, the maximum file size is based on a GPU limit. The maximum tile size may be 1024 pixels by 1024 pixels. The image data may include a plurality of pixels including 16 bits per pixel.

In one or more embodiments, the plurality of reduced resolutions include resolutions of ($½, \ldots ½^n$), where n is an integer greater than or equal to 1.

In one or more embodiments, the at least one overlapping image includes a plurality of tiles at a new resolution, where the new resolution is the next higher resolution generated compared to the resolution currently displayed on the display device.

In one or more embodiments, the steps further include receiving a request from the computing device to access data corresponding to an updated image display window, determining at least one updated image to send the computing device based on the updated image display window, where the at least one updated image is selected from the plurality of high-resolution tiles and the plurality of reduced resolution tiles, and sending the at least one updated image to the computing device for display in real time.

The image data may include full-resolution medical imaging data. For example, the data set may comply with the Digital Imaging and Communications in Medicine (DICOM) file format definition. The image data may include video data.

In one or more embodiments, the steps further include providing metadata associated with the data set to the computing device.

The steps may also include receiving new metadata from the computing device, and associating the new metadata with the data set.

The steps may also include sending the computing device background data including unsent image data selected from the plurality of high-resolution tiles and the plurality of reduced-resolution tiles.

One or more embodiments of the system and method for image data management described herein enable a computer-readable medium including computer-readable instructions for displaying image data, where execution of the computer-readable instructions by one or more processors causes the one or more processors to carry out steps.

One of the steps carried out by the one or more processors is sending a request to access medical imaging data from a server.

Another step carried out by the one or more processors is receiving an initial image. In one or more embodiments, the initial image is a scaled full image of the medical imaging data, where the reduced resolution image is limited in size based on a GPU limit.

Another step carried out by the one or more processors is processing the initial image on a graphical processor unit (GPU).

Another step carried out by the one or more processors is displaying a displayed image based on initial image on a display device.

Another step carried out by the one or more processors is receiving a plurality of overlap images from the server, where a resolution of the plurality of overlap images is higher than a resolution of the scaled full image, and where the plurality of overlap images is limited in size.

Another step carried out by the one or more processors is processing the plurality of overlap images in series on the GPU to update at least a portion of the displayed image with at least a portion of an overlap image.

Another step carried out by the one or more processors is accepting input from a user including a change in a view of the medical imaging data.

Another step carried out by the one or more processors is sending a request including the change in the view to the server.

Another step carried out by the one or more processors is receiving at least one additional image from the server, where the at least one additional image is limited in size.

Another step carried out by the one or more processors is processing the at least one additional image in series on the GPU to update at least a portion of the displayed image with at least a portion of an overlap image, where the portion of the overlap image is determined based on the change in the view.

In one or more embodiments, the plurality of overlap images and the at least one additional image are limited in size based on a GPU limit. The plurality of overlap images may be limited in size based on a GPU limit. The plurality of overlap images may be limited in size to 1024 pixels by 1024 pixels at 16-bits per pixel.

In one or more embodiments, the medical imaging data complies with the Digital Imaging and Communications in Medicine (DICOM) file format definition. The medical imaging data may include video data.

The steps may also include receiving and displaying metadata associated with a portion of the medical imaging data associated with the displayed image.

In one or more embodiments, the steps further include accepting new metadata from the user, and sending the new metadata to the serve. The steps may also include storing at least one of the plurality of overlap images and the at least one additional image in a local memory store, and processing at least one stored image on the GPU to update at least a portion of the displayed image based on the change in the view.

The steps may also include receiving background data including unsent image data selected from the image data, the plurality of high-resolution tiles, and the plurality of reduced-resolution tiles.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

Systems and methods for the image data management will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. Furthermore, although steps or processes are set forth in an exemplary order to provide an understanding of one or more systems and methods, the exemplary order is not meant to be limiting. One of ordinary kill in the art would recognize that the steps or processes may be performed in a different order, and that one or more steps or processes may be performed simultaneously or in multiple process flows without departing from the spirit or the scope of the invention. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
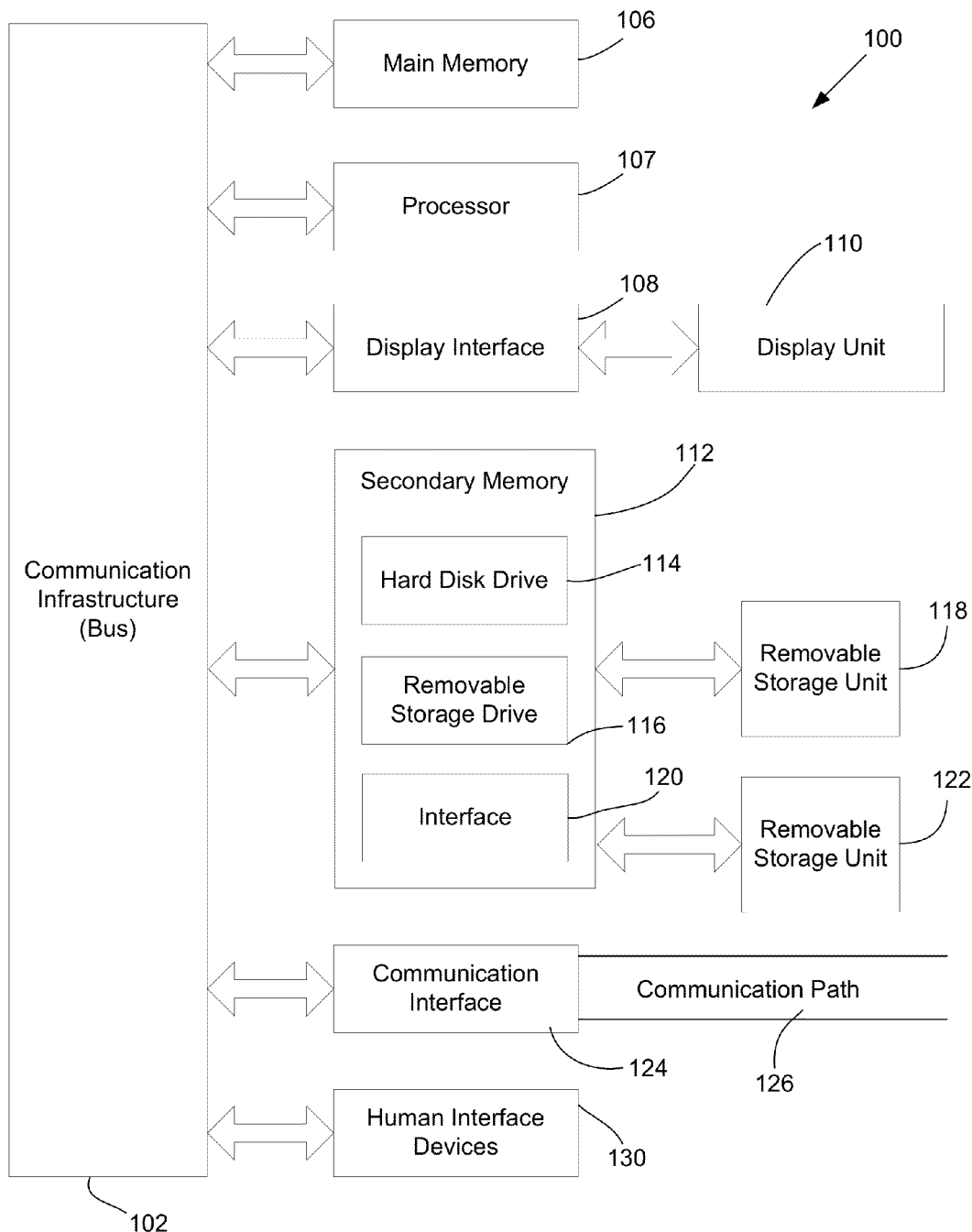
FIG. 1 illustrates a general-purpose computer and peripherals that when programmed as described herein may operate as a specially programmed computer in accordance with one or more embodiments of systems and methods for image data management.

FIG. 1 illustrates a general-purpose computer and peripherals that when programmed as described herein may operate as a specially programmed computer in accordance with one or more embodiments of systems and methods for image data management.

At least one processor 107 may be coupled to bi-directional communication infrastructure 102 such as communication infrastructure system bus 102. Communication infrastructure 102 may generally be a system bus that provides an interface to the other components in the general-purpose computer system such as processor 107, main memory 106, display interface 108, secondary memory 112 and/or communication interface 124.

The at least one processor may include at least one graphics processing unit (GPU). As used herein, the term GPU refers to any specialized circuit design to accelerate image processing in a frame buffer for output. A GPU may be present on a video card, a motherboard, or as a component of a CPU.

Main memory 106 may provide a computer readable medium for accessing and executed stored data and applications. Display interface 108 may communicate with display unit 110 that may be utilized to display outputs to the user of the specially-programmed computer system. Display unit 110 may comprise one or more monitors that may visually depict aspects of the computer program to the user. Main memory 106 and display interface 108 may be coupled to communication infrastructure 102, which may serve as the interface point to secondary memory 112 and communication interface 124. Secondary memory 112 may provide additional memory resources beyond main memory 106, and may generally function as a storage location for computer programs to be executed by processor 107. Either fixed or removable computer-readable media may serve as Secondary memory 112. Secondary memory 112 may comprise, for example, hard disk 114 and removable storage drive 116 that may have an associated removable storage unit 118. There may be multiple sources of secondary memory 112 and systems implementing the solutions described in this disclosure may be configured as needed to support the data storage requirements of the user and the methods described herein. Secondary memory 112 may also comprise interface 120 that serves as an interface point to additional storage such as removable storage unit 122. Numerous types of data storage devices may serve as repositories for data utilized by the specially programmed computer system. For example, magnetic, optical or magnetic-optical storage systems, or any other available mass storage technology that provides a repository for digital information may be used.

Communication interface 124 may be coupled to communication infrastructure 102 and may serve as a conduit for data destined for or received from communication path 126. A network interface card (NIC) is an example of the type of device that once coupled to communication infrastructure 102 may provide a mechanism for transporting data to communication path 126. Computer networks such Local Area Networks (LAN), Wide Area Networks (WAN), Wireless networks, optical networks, distributed networks, the Internet or any combination thereof are some examples of the type of communication paths that may be utilized by the specially program computer system. Communication path 126 may comprise any type of telecommunication network or interconnection fabric that can transport data to and from communication interface 124.

To facilitate user interaction with the specially programmed computer system, one or more human interface devices (HID) 130 may be provided. Some examples of HIDs that enable users to input commands or data to the specially programmed computer may comprise a keyboard, mouse, touch screen devices, microphones or other audio interface devices, motion sensors or the like, as well as any other device able to accept any kind of human input and in turn communicate that input to processor 107 to trigger one or more responses from the specially programmed computer are within the scope of the system disclosed herein.

While FIG. 1 depicts a physical device, the scope of the system may also encompass a virtual device, virtual machine or simulator embodied in one or more computer programs executing on a computer or computer system and acting or providing a computer system environment compatible with the methods and processes of this disclosure. In one or more embodiments, the system may also encompass a cloud computing system or any other system where shared resources, such as hardware, applications, data, or any other resource are made available on demand over the Internet or any other network. In one or more embodiments, the system may also encompass parallel systems, multi-processor systems, multi-core processors, and/or any combination thereof. Where a virtual machine, process, device or otherwise performs substantially similarly to that of a physical computer system, such a virtual platform will also fall within the scope of disclosure provided herein, notwithstanding the description herein of a physical system such as that in FIG. 1.

Figure 2:
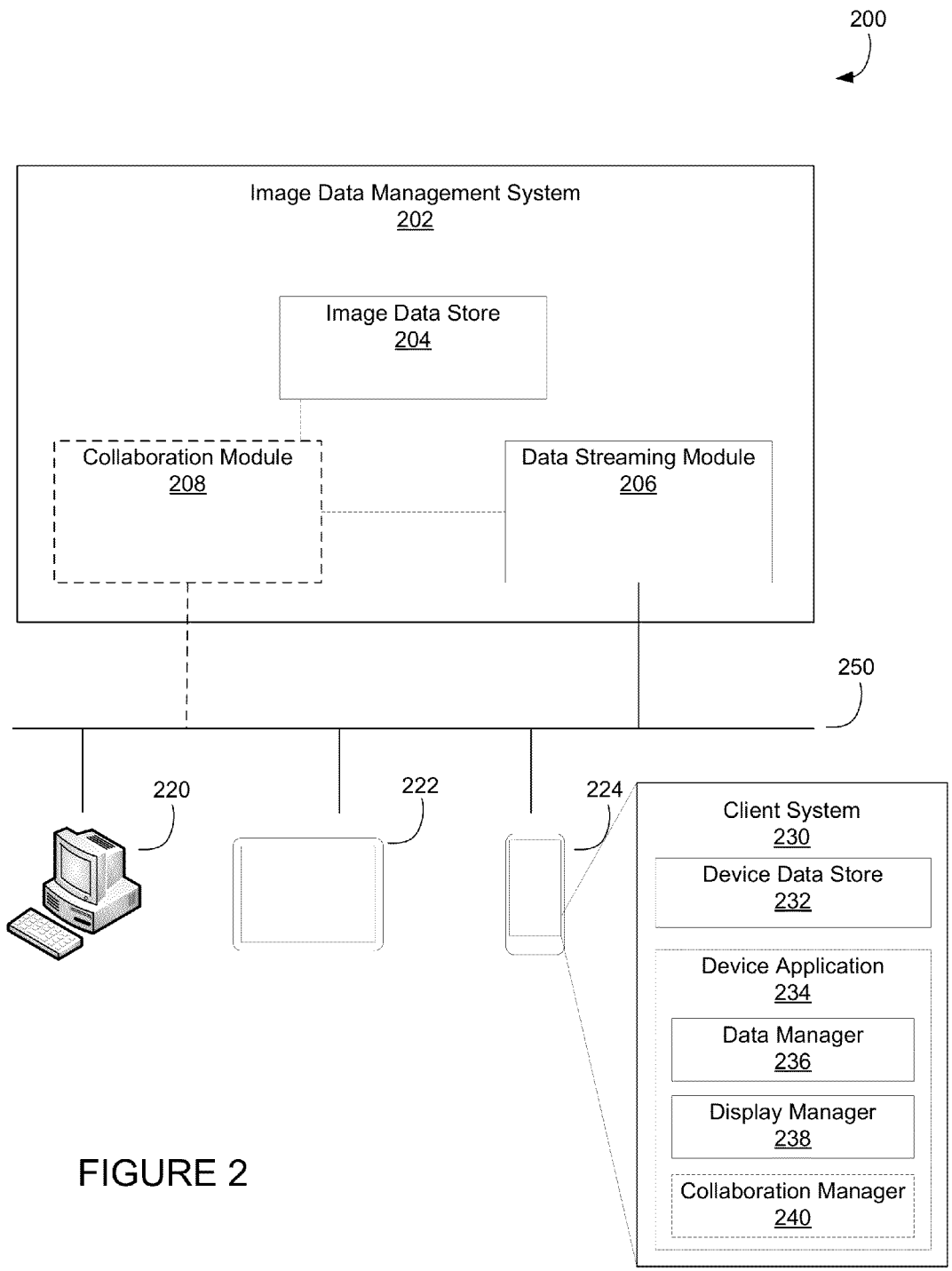
FIG. 2 illustrates an exemplary image data management system in accordance with one or more embodiments of systems and methods for image data management.

FIG. 2 illustrates an exemplary image data management system in accordance with one or more embodiments of systems and methods for image data management.

System 200 includes image data management system 202. Image data management system 202 includes software and hardware resources for implementing systems and methods for image data management described herein.

Image data management system 202 includes image data store 204. Image data store 204 is configured to store one or more tiled representation of a data set that includes image data at high resolution. The tiled representation includes a plurality of high-resolution tiles and a plurality of reduced resolution tiles. None of the high-resolution tiles and reduced resolution tiles is larger than the maximum tile size. The maximum tile size may be based on an image size or a file size. In one or more embodiments, the maximum tile size is based on a GPU limitation.

The image data may include video data. In one or more embodiments, the data set includes full resolution medical imaging data. The medical imaging data may include any medical imaging data that complies with the Digital Imaging and Communications in Medicine (DICOM) file format definition. DICOM is a standard for handling, storing, printing and transmitting information in medical imaging. Medical imaging data that may be stored in a DICOM data set includes x-ray, angiogram, MRI, CT, ultrasound, nuclear, and any other type of medical imaging data compatible with the DICOM standard.

Image data management system 202 further includes data streaming module 206. Data streaming module 206 is configured to deliver at least a portion of a tiled representation stored in image data store 204 to one or more client devices 220-224. Data streaming module 206 may be configured to provide data to one or more client devices 220-204 based on a request from a client device.

Image data management system 202 optionally includes collaboration module 208. Collaboration module 208 is configured to manage one or more collaboration sessions between a plurality of client devices 220-224. An exemplary collaboration session illustrated in FIG. 13.

Although the elements of image data management system 202 (e.g. image data store 204, data streaming module 206 and collaboration module 208) are shown as distinct modules for purposes of illustration, one of ordinary skill in the art would recognize that these elements of image data management system 202 may be implemented in an integrated manner without departing from the spirit or the scope of the invention.

System 200 further includes one or more client devices 220-224. Client devices 220-224 may include any computing device, including any general-purpose computer and/or any mobile computing device. For example, client devices to 220-224 may include a desktop computer, a laptop computer, a mobile tablet device, a PDA, a mobile telephone, a smart phone, or any other device capable of implementing the systems and methods for image data management described herein. In one or more embodiments, client devices 220-224 include one or more network-enabled mobile computing devices with a GPU.

Client devices 220-224 are configured to implement client system 230. Client system 230 includes software and hardware resources for implementing systems and methods for image data management described herein.

Client system 230 includes device data store 232. Device data store 232 is configured to store data corresponding to one or more tiled representations of a data set that includes image data at high-resolution. Device data store 232 may also store metadata corresponding to one or more tiled representations. In one or more embodiments, device data store 232 resides in a secondary memory of a client device. A total size limit of device data store 232 may be imposed by device application 234 and/or an external limit to client system 230, such as an operating system limit of client device 224.

Client system 230 further includes device application 234. Device application 234 may include computer-readable instructions stored on a tangible computer-readable medium of a client device.

Device application 234 includes data manager 236. Data manager 236 is configured to communicate with image data system 202 to request and receive at least a portion of a tiled representation of a data set that includes image data at high-resolution. The tiled representation includes a plurality of high-resolution tiles and a plurality of reduced resolution tiles. The tiled representation may include full-resolution tiles and reduced-resolution tiles at the original bit depth of the high-resolution image data. None of the high-resolution tiles and reduced resolution tiles is larger than the maximum tile size. The maximum tile size may be based on an image size or a file size. In one or more embodiments, the maximum tile size is based on a GPU limitation.

The image data may include video data. In one or more embodiments, the data set includes full resolution medical imaging data. The medical imaging data may include any medical imaging data that complies with the DICOM file format definition.

Data manager 236 may be configured to process at least a portion of multiple tiled representations, each tiled representation corresponding to a different data set. In one or more embodiments, data manager 236 is configured to store at least a portion of one or more DICOM files. Data manager 236 may also be configured to process metadata associated with a tiled representation.

Data manager 236 may store data corresponding to one or more tiled representations in device data store 232. In one or more embodiments, data manager 236 is configured to manage the storage of data in device data store 232. Data manager 236 may manage the storage of data taking into consideration a total size limit of device data store, including any size limit imposed by device application 234 or a size limit external to client system 230.

Device application 234 further includes display manager 238. Display manager 238 is configured to manage the display of data received from image data management system 202 and/or image data stored in device data store 232. Display manager 238 constructs a final image for display on a display device of the client device. In one or more embodiments, display manager 238 interacts with a GPU of the client device to display or update either the entire displayed image or one or more portions of the displayed image. Display manager 238 may be configured to modify one or tiles to reduce a bit depth of the tile based on a GPU limitation.

The displayed image corresponds to an image display window. The image display window is used to determine the appropriate portion of the data set to currently display. Device application 234 may access user input received from a user interface provided to a user of the client device to determine the current image display window. In one or more embodiments, display manager 238 manages, constructs and/or updates the final image for display based on the image display window.

Optionally, device application 234 further includes collaboration manager 240. Collaboration manager 240 is configured to manage one or more collaboration sessions between a plurality of client devices. An exemplary collaboration session illustrated in FIG. 13.

Although the elements of client system 230 (e.g. device data store 230, device application 234, data manager 236, display manager 238 and collaboration manager 240) are shown as distinct modules for purposes of illustration, one of ordinary skill in the art would recognize that these elements of client system 230 may be implemented in an integrated manner without departing from the spirit or the scope of the invention.

System 200 further includes network 250. Image data management system 202 communicates with client devices 220-224 over network 250. Network 250 may include one or more Local Area Networks (LAN), Wide Area Networks (WAN), wireless networks, cellular data networks, optical networks, distributed networks, the Internet, or any combination thereof.

Figure 3A:
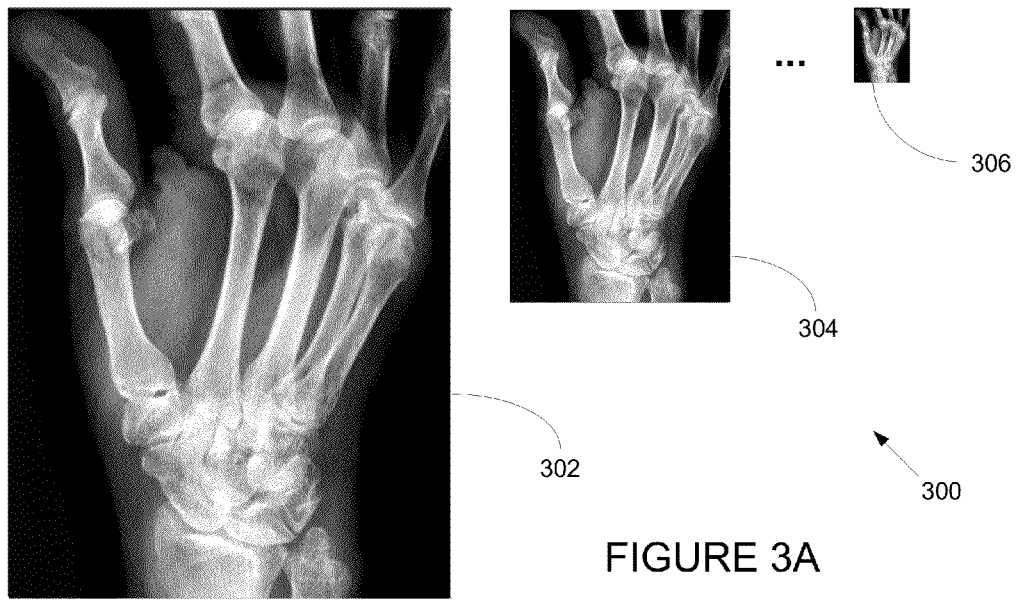
FIG. 3A illustrates exemplary scaled full images in accordance with one or more embodiments of systems and methods for image data management.

FIG. 3A illustrates exemplary scaled full images in accordance with one or more embodiments of systems and methods for image data management. Scaled full images 300 include full resolution image 302. Full resolution image 302 is a full representation of high-resolution image data. Full resolution image 302 has the highest resolution of scaled full images 300. In one or more embodiments, full resolution image 302 may have the same resolution as the high-resolution image data, enabling image data to be provided at the original resolution in accordance with one or more systems and methods for image data management. Alternatively, full resolution image 302 may have a lower resolution may be used compared to the original image data, as long as full resolution image 302 has a higher resolution output of scaled full images 300. In this case, full resolution image 302 has a maximum resolution that one or more systems and methods for image data management is configured to provide.

Scaled full images 300 further include at least one reduced resolution image 304-306. Reduced resolution images 304-306 are full representations of high-resolution image data. Reduced resolution images 304-306 have a lower resolution relative to full resolution image 302. In one or more embodiments, the lowest resolution image 306 is limited in size based on a GPU limitation. The at least one reduced representation 304-306 may included resolutions of $1/m, 1/(m^2), \ldots 1/m^n$, where n is an integer greater than or equal to 1 and where m is a real number greater than 1. The at least one reduced representation 304-306 may include resolutions of $1/2 \ldots 1/2^n$, where n is an integer greater than or equal to 1.

In one or more embodiments, scaled full images 300 include a plurality of images that represent video data. As used herein, the term "image" includes any graphical representation, including any multi-framed graphical representation as well as any single-frame graphical representation. In one or more embodiments, scaled full images 300 represent medical imaging data. The medical imaging data may include any medical imaging data that complies with the DICOM file format definition.

Figure 3B:
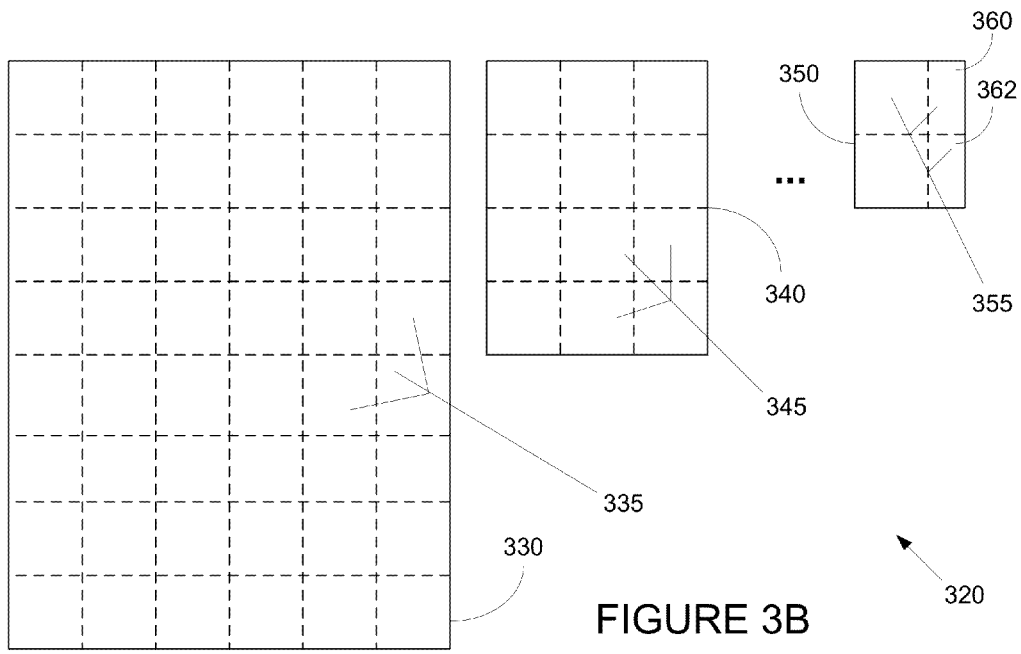
FIG. 3B illustrates exemplary high-resolution tiles and reduced-resolution tiles in accordance with one or more embodiments of systems and methods for image data management.

FIG. 3B illustrates exemplary high-resolution tiles and reduced-resolution tiles in accordance with one or more embodiments of systems and methods for image data management.

Tiled representation 320 is a tiled representation of high-resolution image data. Tiled representation 320 includes high-resolution tiles 335 and reduced-resolution tiles 345, 355 and 362. Together, individual high-resolution tiles 335 form a full representation 330 of high-resolution image data. In one or more embodiments, full representation 330 may have the same resolution as the high-resolution image data. Alternatively, full representation 330 may have a lower resolution may be used compared to the original high-resolution image data, but a higher resolution then reduced representations 340, 350 and 360. In one or more embodiments, individual full resolution tiles 335 are generated based on a full resolution image, such as full resolution image 302. Full-resolution tiles 335 may include tiles at the original bit depth of the high-resolution image data.

Reduced resolution tiles 345, 355 and 362 correspond to at least one reduced representation 340, 350 and 360. In one or more embodiments, individual reduced resolution tiles 345, 355 and 362 are generated based on at least one reduced resolution image, such as reduced resolution images 304-306. Reduced resolution tiles 345, 355 and 362 may include tiles at the original bit depth of the high-resolution image data.

The at least one reduced representation 340, 350 and 360 may include resolutions of $1/2 \ldots 1/2^n$, where n is an integer greater than or equal to 1. In one or more embodiments, reduced-resolution tiles are generated for reduced representations 340, 350 and 360 such that the smallest reduced representation 360 is made up of a single tile 362.

In one or more embodiments, none of the high-resolution tiles and/or the reduced-resolution tiles is larger than a maximum tile size. The maximum tile size may be based on an image size or a file size. In one or more embodiments, the maximum tile size is based on a GPU limitation, including a memory limitation, an image size limitation, or any other GPU limitation, including limitations imposed on GPU processing that are external to the GPU. In one or more embodiments, the maximum tile size for a 2D image is 1024×1024. Alternatively, a maximum tile size for a 2D image may be set at 2048×2048, or any other limit based on a GPU limitation. The maximum file size may also be set by a memory size. For example, in one or more embodiments, the maximum file size is about 5 MB. Alternatively, the tile may exceed a GPU limitation when a tile is at a current bit depth, but may meet a GPU limitation when the bit depth is reduced.

High-resolution tiles 335 and/or reduced-resolution tiles 345, 355 and 362 may include one or more border tiles 362-372. Border tiles 362-372 represent tiles containing less information than the maximum tile size. One of ordinary skill in the art will recognize that any method suitable for handling partial tiling may be used without departing from the spirit or the scope of the invention.

Figure 4:
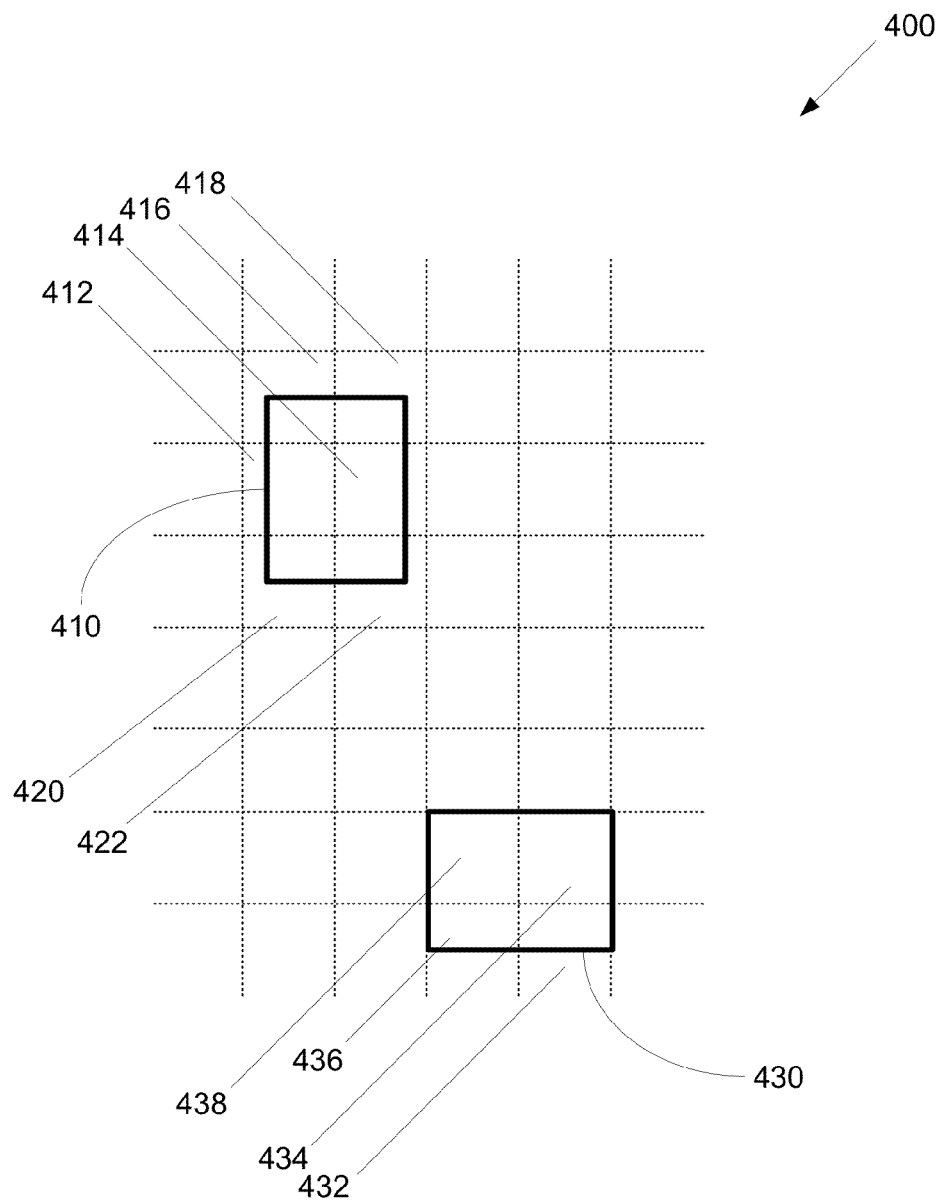
FIG. 4 illustrates exemplary image display windows in accordance with one or more embodiments of systems and methods for image data management.

FIG. 4 illustrates exemplary image display windows in accordance with one or more embodiments of systems and methods for image data management. A plurality of tiles 400 is illustrated with exemplary image display windows superimposed. Tiles 400 are arranged to form a representation of high-resolution image data at a set resolution. Image display window 410 and 430 correspond to a viewable area to be displayed on a display device of a client device. The client device is configured to allow a user to move the viewable area to be displayed on the display device. In one or more embodiments, the client device is configured to change an orientation of the viewable area to be displayed on the display device. For at least these reasons, image display windows 410-430 may change position and/or orientation with respect to tiles 400.

For example, image display window 410 corresponds to a viewable area in a portrait orientation. A displayable image corresponding to image display window 410 is constructed from a subset of the plurality of tiles 412-422. The subset of the plurality of tiles, or overlap images 412-422, overlap with image display window 410 when tiles 400 are arranged to form the representation of the high-resolution image data.

The displayable image may be constructed by either a server of the image data management system or the client device. In one or more embodiments, the displayable image is constructed by a GPU of the client device by individually processing overlapping images 412-422, where overlap images 412-422 are limited in size based on a GPU limitation. In one or more embodiments, overlap images 412-422 may exceed a GPU limitation at a current bit depth; processing the overlap images 412 to reduce a bit depth may bring the overlap images 412-422 within the GPU limitation. The bit depth may be selectively reduced to retain a specific subset of information present in the original overlap image. The GPU limitation may include a memory limitation, an image size limitation, or any other GPU limitation, including limitations imposed on GPU processing that are external to the GPU. For example, the GPU may be configured to process overlap images 412-422 in series, updating at least a portion of the displayable image with at least a portion of each overlap image as it is processed.

Image display window 430 corresponds to a viewable area in a landscape orientation. A display image corresponding to image display window 430 is constructed from a subset of the plurality of tiles 432-438. The subset of the plurality of tiles, or overlap images 432-438, overlap with image display window 430 when tiles 400 are arranged to form the representation of the high-resolution image data.

Figure 5:
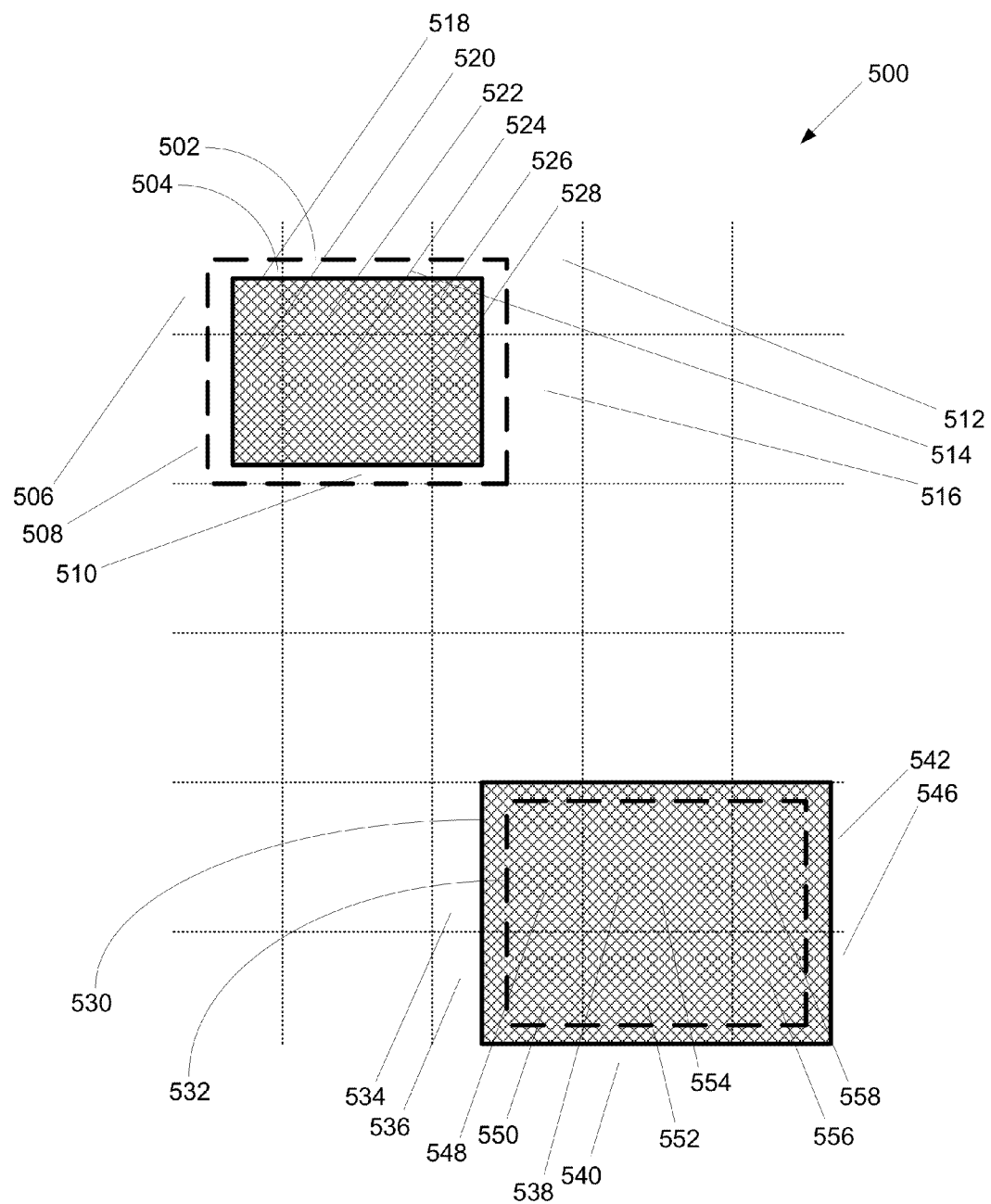
FIG. 5 illustrates exemplary image display windows in accordance with one or more embodiments of systems and methods for image data management.

FIG. 5 illustrates exemplary image display windows in accordance with one or more embodiments of systems and methods for image data management. A plurality of tiles 500 is illustrated with exemplary image display windows superimposed. Tiles 500 are arranged to form a representation of high-resolution image data at a set resolution.

In one or more embodiments, the user of the client device may change a resolution of the displayable image. When the resolution changes significantly, tiles of a different resolution may be provided. A user may be allowed to change a resolution of the displayable image to a resolution other than a resolution of a high-resolution tile or any reduced resolution tiles. In this case, upscaling or downscaling operations may be performed. In one or more embodiments, upscaling or downscaling operations are performed on a client device. One of ordinary skill in the art would recognize that many methods may be used for rescaling images without departing from the spirit or the scope of the invention.

Resized image display window 504 corresponds to a displayable area on a client device when a user wishes to view the image data at a greater resolution than the resolution of tiles 500. Reference window 504 is shown to illustrate the size of an image display window that is used when a user views the image data at an exact resolution of the resolution of tiles 500. A displayable image is generated from areas 518-528 of overlap images 506-516. Overlap images 506-516 comprise a subset of tiles 500 that overlap with resized image display window 504. The displayable image may be constructed by either a server of the image data management system or the client device. In one or more embodiments, the displayable image is constructed by a GPU of the client device by individually processing overlapping images 506-516, where overlap images 506-516 are limited in size based on a GPU limitation. The GPU limitation may include a memory limitation, an image size limitation, or any other GPU limitation, including limitations imposed on GPU processing that are external to the GPU. For example, the GPU may be configured to process overlap images 412-422 in series, updating at least a portion of the displayable image with at least a portion of each overlap image as it is processed.

Resized image display window 530 corresponds to a displayable area on a client device when a user wishes to view the image data at a lower resolution than the resolution of tiles 500. Reference window 532 is shown to illustrate the size of an image display window that is used when a user views the image data at an exact resolution of the resolution of tiles 500. A displayable image is generated from areas 548-558 of overlap images 534-546. Overlap images 534-546 comprise a subset of tiles 500 that overlap with resized image display window 530. The displayable image may be constructed by either a server of the image data management system or the client device. In one or more embodiments, the displayable image is constructed by a GPU of the client device by individually processing overlapping images 534-546, where overlap images 534-546 are limited in size based on a GPU limitation. The GPU limitation may include a memory limitation, an image size limitation, or any other GPU limitation, including limitations imposed on GPU processing that are external to the GPU. For example, the GPU may be configured to process overlap images 534-546 in series, updating at least a portion of the displayable image with at least a portion of each overlap image as it is processed.

Figure 6:
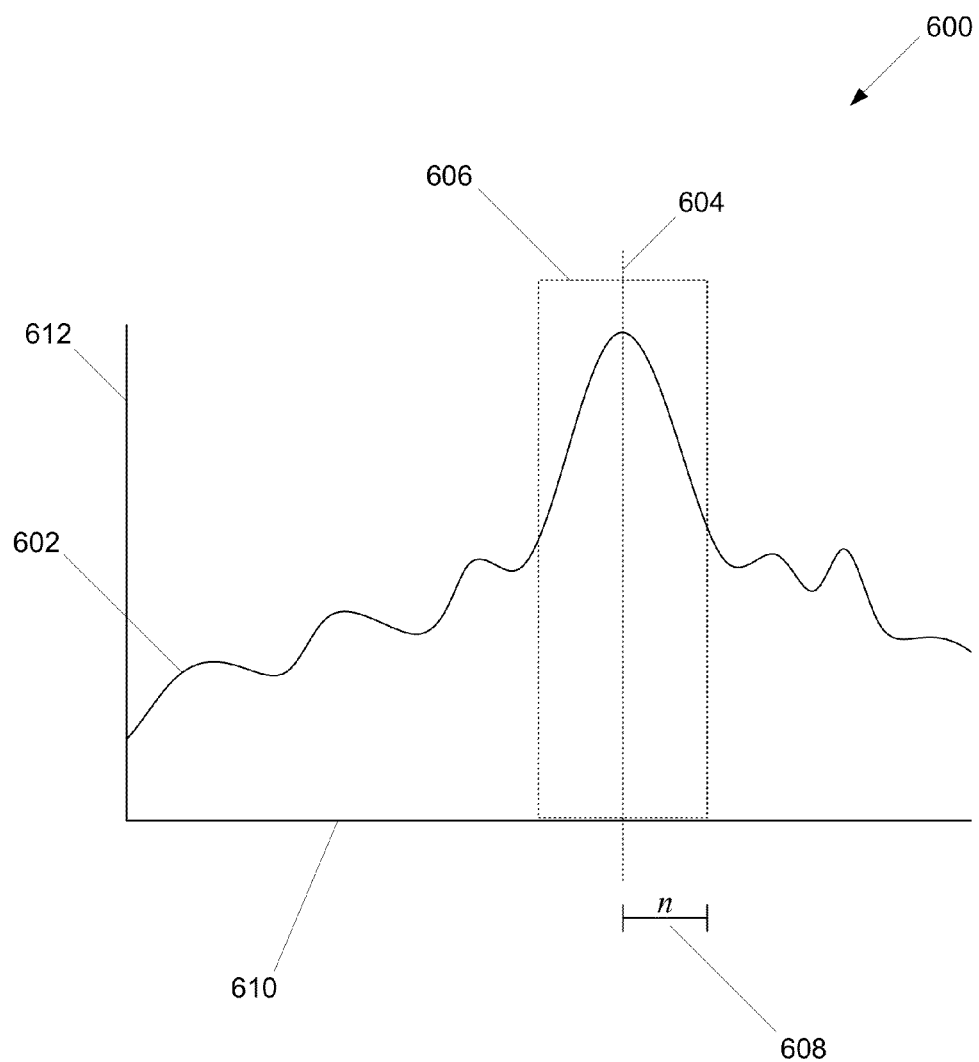
FIG. 6 illustrates an exemplary use of windowing in accordance with one or more embodiments of systems and methods for image data management.

FIG. 6 illustrates an exemplary use of windowing in accordance with one or more embodiments of systems and methods for image data management.

In one or more embodiments, GPU limitations may affect an image dimension as well as other image constraints. For example, in one or more embodiments, a bit depth of an image may be modified to accommodate one or more GPU limitations.

In one or more embodiments, providing a user high-resolution image data involves retaining bit depth information present in the original high-resolution image data, including medical imaging data such as data that complies with the DICOM file format definition. In one or more embodiments, the tiled representation comprises full-resolution tiles and reduced-resolution tiles include tiles at the original bit depth of the high-resolution image data. One of ordinary skill in the art would appreciate that many methods may be used to reduce a bit depth to accommodate a GPU limitation without losing the higher bit depth information. An exemplary windowing procedure is shown in FIG. 6 for illustrative purposes.

Histogram 600 corresponds to bit depth information 602 for an exemplary image. Histogram 600 has x-axis 610 and y-axis 612. X-axis 610 corresponds to a bit depth of the exemplary image. The bit depth is any bit depth suitable for any high-resolution image data. For example, a typical bit depth of 16 may be used, leading to an x-axis 610 range of [0, 65536], [−32768, 32767], or any other range equivalent to a bit depth of 16.

If a lower bit depth is desirable based on the GPU limitation, a windowing technique may be used to modify the exemplary image before GPU processing. Based on one or more user selections, window 606 is determined. The bit depth information 602 within window 606 is used to generate a modified image with the lower bit depth. The pixel values may be normalized, such as to a range of between 0 and 1. The modified image contains all of the bit depth information within window 606. The modified image is processed by the GPU to construct or modify a displayable image on the client device.

In one or more embodiments, window 606 is determined based on a median value 604 and a radius value 608. The median value 604 and a radius value 608 may be modified based on one or more selections of a user viewing the high-resolution image data.

In one or more embodiments, the server transmits an exemplary image with the original bit depth to the client device, and the client device modifies the exemplary image before GPU processing. The client device may save the exemplary image with the original bit depth such that the windowing process may be repeated by the client device when a user changes windows 606.

Figure 7:
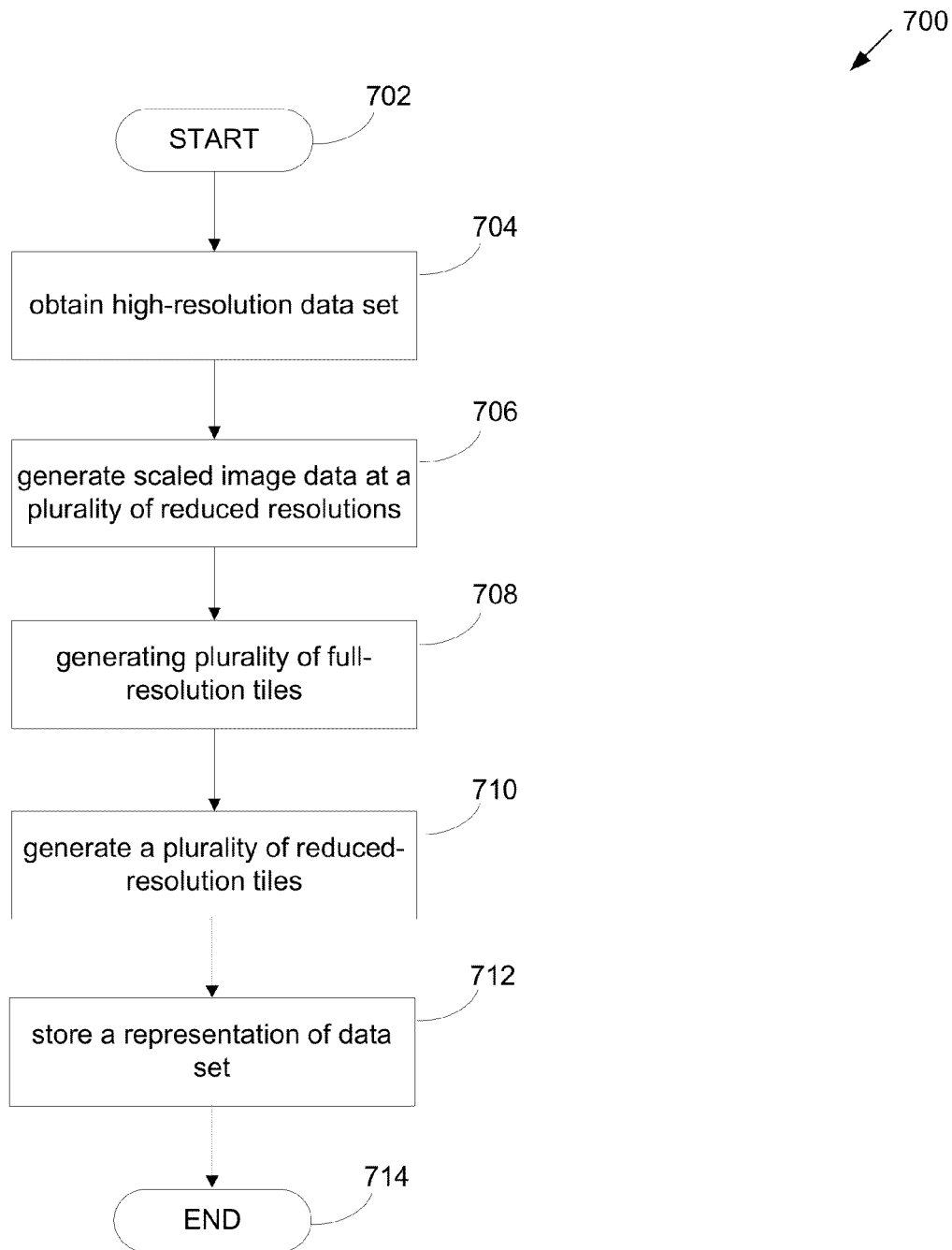
FIG. 7 is a flowchart for an exemplary method for processing image data in accordance with one or more embodiments of systems and methods for image data management.

FIG. 7 is a flowchart for an exemplary method for processing image data in accordance with one or more embodiments of systems and methods for image data management. Process 700 begins at step 702.

Processing continues to step 704, where a high-resolution data set is obtained. The dataset includes high-resolution image data. The image data may include video data. In one or more embodiments, the data set includes full resolution medical imaging data. The medical imaging data may include any medical imaging data that complies with the DICOM file format definition.

Processing continues to step 706, where scaled image data is generated. A plurality of scaled full images is generated, where each scaled full image is a full representation of the image data. The scaled full images include a full resolution image and at least one reduced resolution image. The scaled full images may include a lowest resolution image with a size limitation based on a GPU limitation. The plurality of reduced resolutions may be reduced by a factor of m (e.g. $1/m$, $1/(m^2)$, ... $1/m^n$, where n is an integer greater than or equal to 1 and where m is a real number greater than 1). In one or more embodiments, the plurality of reduced resolutions is reduced by 2 in each dimension (e.g. $\frac{1}{2}$, $\frac{1}{4}$, ... $\frac{1}{2^n}$, where n is an integer greater than or equal to 1).

Processing continues to step 708, where a plurality of full-resolution tiles is generated based on the full resolution image. In one or more embodiments, none of the high-resolution tiles are larger than the maximum tile size. The maximum tile size may be based on an image size or a file size. In one or more embodiments, the maximum tile size is based on a GPU limitation, including a memory limitation, an image size limitation, or any other GPU limitation, including limitations imposed on GPU processing that are external to the GPU. In one or more embodiments, the maximum tile size for a 2D image is 1024×1024. Alternatively, a maximum tile size for a 2D image may be set at 2048×2048, or any other limit based on a GPU limitation. The maximum file size may also be set by a memory size. For example, in one or more embodiments, the maximum file size is about 5 MB. Alternatively, the tile may exceed a GPU limitation when a tile is at a current bit depth, but may meet a GPU limitation when the bit depth is reduced.

Processing continues to step 710, where a plurality of reduced-resolution tiles are generated based on the at least one reduced resolution image. Processing continues to step 708, where a plurality of full-resolution tiles is generated. In one or more embodiments, none of the high-resolution tiles are larger than the maximum tile size. The maximum tile size may be based on an image size or a file size. In one or more embodiments, the maximum tile size is based on a GPU limitation, including a memory limitation, an image size limitation, or any other GPU limitation, including limitations imposed on GPU processing that are external to the GPU. In one or more embodiments, the maximum tile size for a 2D image is 1024×1024. Alternatively, a maximum tile size for a 2D image may be set at 2048×2048, or any other limit based on a GPU limitation. Alternatively, the tile may exceed a GPU limitation when a tile is at a current bit depth, but may meet a GPU limitation when the bit depth is reduced.

Processing continues to step 712, where a representation of the data set is stored. The tiled representation of the data set includes the plurality of scaled full images at a plurality of resolutions, the plurality of high-resolution tiles, and the plurality of reduced resolution tiles.

The data set may include metadata associated with the image. The metadata may be associated with specific pixels, areas or other features of the high-resolution image data. In one or more embodiments, the tiled representation includes metadata associated with the image. The metadata may be associated with high-resolution tiles, reduced resolution tiles, and/or scaled full images that contain features of the high-resolution image data associated with the metadata. In one or more embodiments, any metadata specified in the DICOM standard may be associated with high-resolution tiles, reduced resolution tiles, and/or scaled full images.

Processing continues to step 714 where process 700 terminates.

Figure 8:
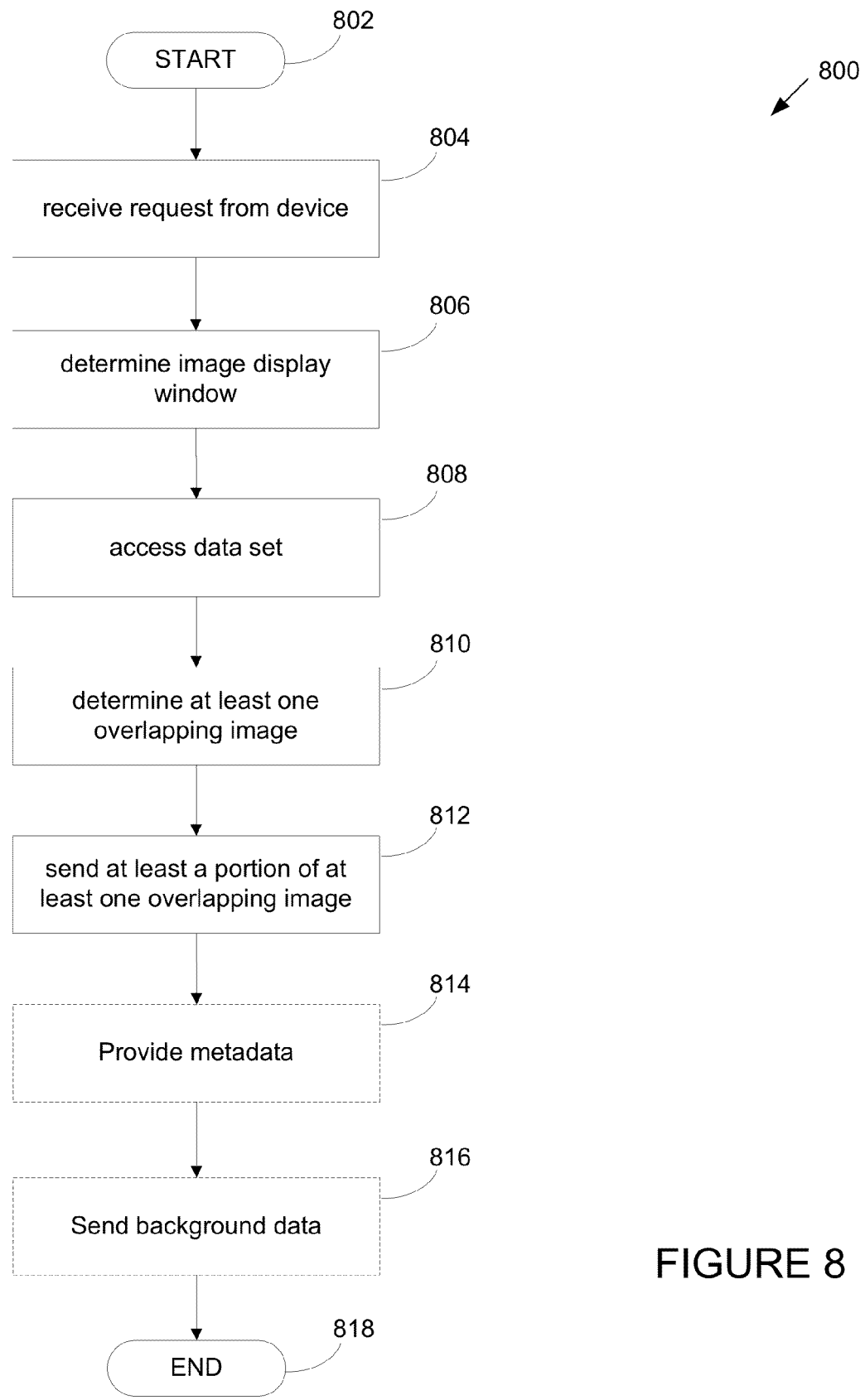
FIG. 8 is a flowchart for an exemplary method for providing image data in accordance with one or more embodiments of systems and methods for image data management.

FIG. 8 is a flowchart for an exemplary method for providing image data in accordance with one or more embodiments of systems and methods for image data management. Process 800 begins at step 802.

Processing continues to step 804, where a request to access a tiled representation of a data set is received from a client device. The tiled representation includes a plurality of high-resolution tiles and a plurality of reduced resolution tiles of high-resolution image data. The plurality of reduced resolutions may reduced by a factor of m (e.g. $1/m$, $1/(m^2)$, ... $1/m^n$, where n is an integer or equal to 1 and where m is a real number greater than 1). The plurality of reduced resolutions tiles may include tiles at least one reduced resolution. In one or more embodiments, the reduced resolutions are $\frac{1}{4}$, ... $\frac{1}{2^n}$, where n is an integer or equal to 1. None of the high-resolution tiles and reduced resolution tiles is larger than the maximum tile size. The maximum tile size may be based on an image size or a file size. In one or more embodiments, the maximum tile size is based on a GPU limitation. In one or more embodiments, the data set includes full resolution medical imaging data, such as data that complies with the Digital Imaging and Communications in Medicine (DICOM) file format definition.

Processing continues to step 806, where an image display window is determined. The image display window is used to determine the appropriate portion of the data set to provide the client device. The image display window corresponds to a viewable area to be displayed on a display device of a client device. The image display window may be determined based on position and dimension information obtained from the client device. The image display window may correspond to a desired resolution, which may be obtained as additional data, or may be calculated based on the image display window.

Processing continues to step 808, where the tiled representation of the data set is accessed. Depending on the desired resolution, the tiles accessed may be from the high-resolution tiles or the reduced resolution tiles of a desired resolution.

Processing continues to step 810, where at least one overlapping image is determined. The at least one overlapping image include tiles of the desired resolution that overlap with the image display window.

Processing continues to step 812, where at least a portion of the at least one overlapping image is sent to the computing device. The entire overlapping image may be sent to the computing device. Alternatively, only the overlapping portion of the overlapping image is sent. In one or more embodiments, the computing device has access to one or more overlapping images from a previous operation or from background data transfer. In this case, one or more overlapping images may not be sent.

Processing continues to optional step 814, where metadata associated with the dataset is provided to the computing device. The metadata may include data that complies with the DICOM file format definition. In one or more embodiments, the metadata provided to the computing device corresponds to metadata that is relevant to a portion of the high-resolution image data that corresponds to the image display window.

Processing continues to optional step 816, where background data is sent. The background data includes the high-resolution tiles and the reduced resolution tiles. The background data may also include metadata associated with the high-resolution image data. In one or more embodiments, background data is sent to the computing device when no other data requests are pending, such as requests based on an image display window. The transmittal of background data may be sent in a prioritized order. For example, a formula may be used to calculate a weight based on the likelihood that the computing device will request the data. The weight may be based on a distance function that takes into account a current image display window position and a current image display window resolution.

Processing continues to step 818, where process 800 terminates.

Figure 9:
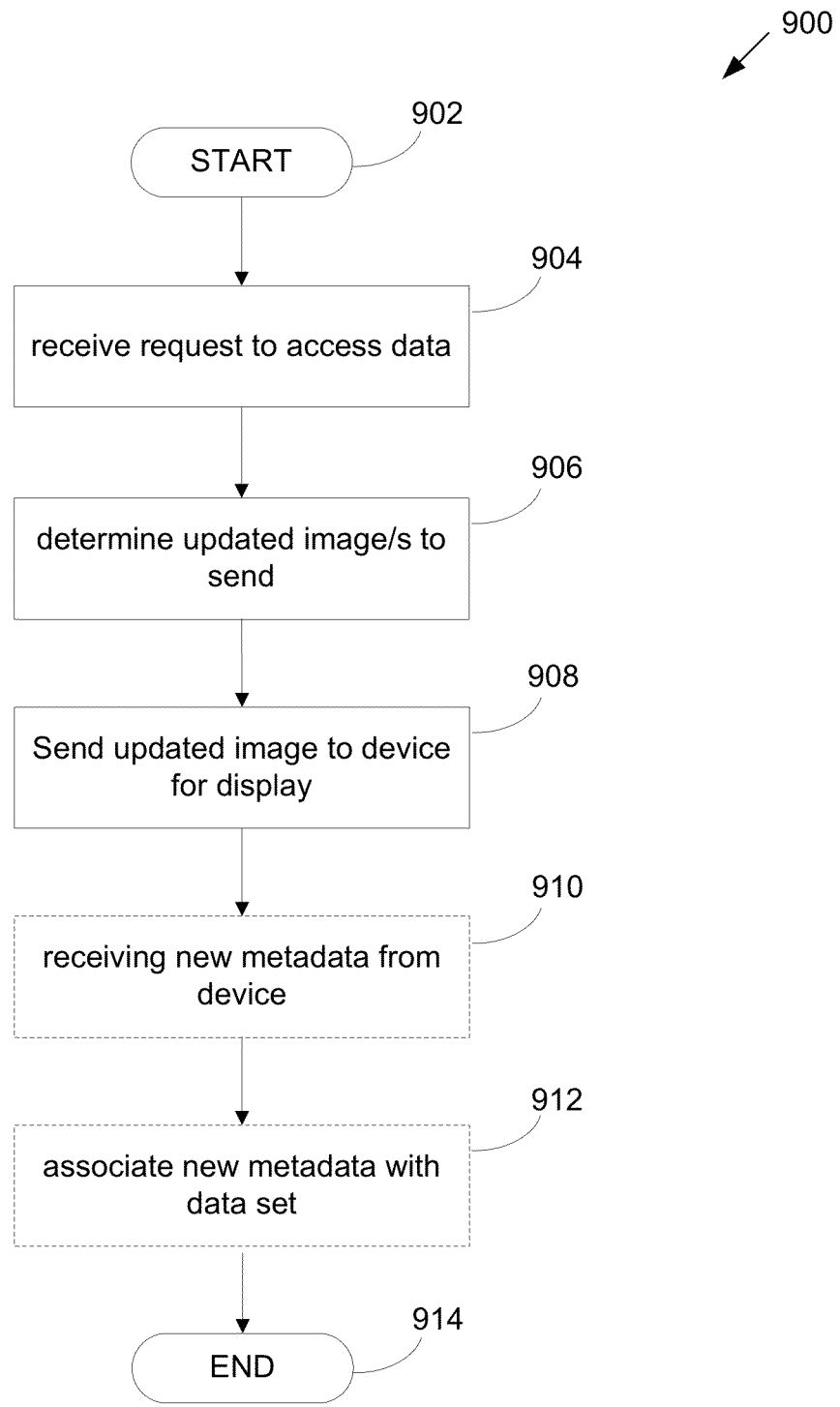
FIG. 9 is a flowchart for an exemplary method for providing image data in accordance with one or more embodiments of systems and methods for image data management.

FIG. 9 is a flowchart for an exemplary method for providing image data in accordance with one or more embodiments of systems and methods for image data management. Process 900 begins at step 902.

Processing continues to step 904, where a request to access data is received. The request received is a request to access data corresponding to an updated image display window. An image display window may be updated based on input by a user of the computing device. For example, a user may attempt to change a position and/or resolution of the image displayed on the computing device.

Processing continues at step 906, where updated images to send are determined. The updated images are determined based on the updated image display window such as a position and/or resolution corresponding to the updated image display window. The updated images may include tiles of the desired resolution that overlap with the updated image display window.

Processing continues to step 908, where the updated images are sent to the device for display. For any updated image, the entire updated image may be sent to the computing device. Alternatively, only the overlapping portion of the updated image is sent. In one or more embodiments, the computing device has access to one or more of the updated images from a previous operation or from background data transfer. In this case, one or more updated images may not be sent.

Processing continues to optional step 910, where metadata associated with the dataset is received from the computing device. The metadata may include data that complies with the DICOM file format definition. In one or more embodiments, the metadata provided to the computing device corresponds to metadata that is relevant to a portion of the high-resolution image data that corresponds to the image display window. The metadata may be added by the user of the computing device. The metadata includes analysis, diagnosis and/or treatment information made by a medical professional, such as a user of the computing device.

Processing continues to optional step 912, where the new metadata is associated with the dataset.

Processing continues to step 914, where process 900 terminates.

Figure 10:
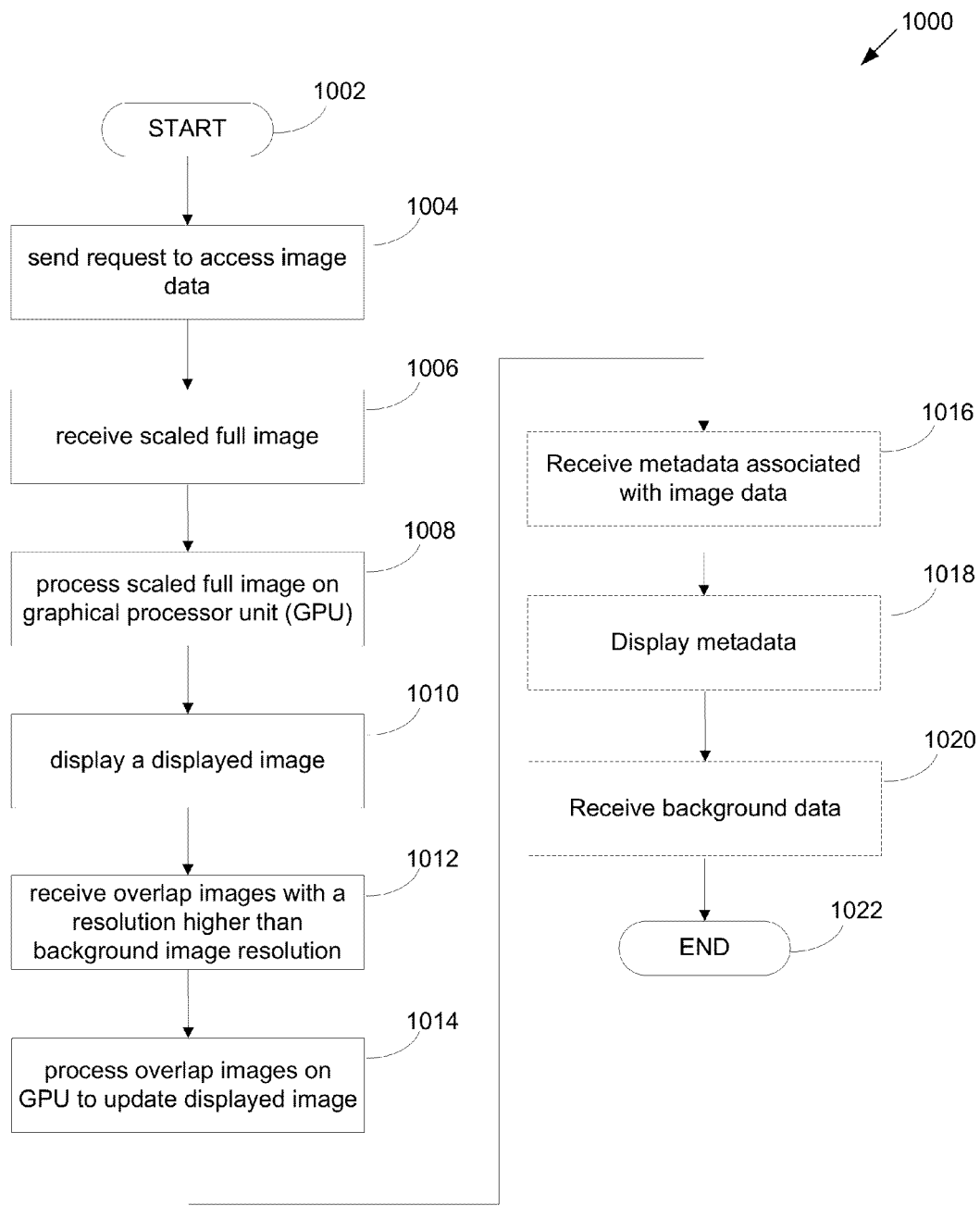
FIG. 10 is a flowchart for an exemplary method for displaying image data in accordance with one or more embodiments of systems and methods for image data management.

FIG. 10 is a flowchart for an exemplary method for displaying image data in accordance with one or more embodiments of systems and methods for image data management. Process 1000 begins at step 1002.

Processing continues to step 1004, where a request to access imaging data from a server is sent. The imaging data may include high-resolution image data and/or video data.

Processing continues to step 1006, where an initial image is received. The initial image may be a scaled full image of the high-resolution image data. In one or more embodiments, the initial image is limited in size based on a GPU limitation.

Processing continues to step 1008, where the initial image is processed on a GPU to generate a displayed image. In one or more embodiments, the initial image is processed to reduce a bit depth of the initial image before processing the initial image on the GPU.

Processing continues to step 1010, where the displayed image is displayed on a display device. The displayed image includes at least a portion of the initial image.

Processing continues to step 1012, where a plurality of overlap images are received from the server. A resolution of the overlap images is higher than the resolution of the initial image received. The overlap images may correspond to an image display window.

Processing continues to step 1014, where the plurality of overlap images are processed on the GPU to update the displayed image. In one or more embodiments, the plurality of overlap images is processed to reduce a bit depth of the overlap images before processing the overlap images on the GPU. The bit depth may be selectively reduced to retain a specific subset of information present in the overlap images. The plurality of overlap images may be processed in series on the GPU based on the limitations of the GPU. When the GPU processes an overlap image, it may use at least a portion of the overlap image to update at least a portion of the displayed image. Upscaling and/or downscaling operations may be performed to update the displayed images.

Processing continues to optional step 1016, where metadata associated with the displayed image is received. In one or more embodiments, the metadata associated with the displayed image includes metadata associated with the overlap images and/or a portion of the high-resolution image data that corresponds to the image display window.

Processing continues to optional step 1018, where the metadata is displayed on the display device.

Processing continues to optional step 1020, where background data is received. In one or more embodiments, the background data includes unsent image data selected from a plurality of high-resolution tiles and the plurality of reduced resolution tiles that make up the tiled representation of a dataset. Background data may be streamed when no active request for other data from the server is pending. The background data may be prioritized based on one or more factors, such as any measure of distance from the current image display window.

Processing continues to step 1022, where process 1000 terminates.

Figure 11:
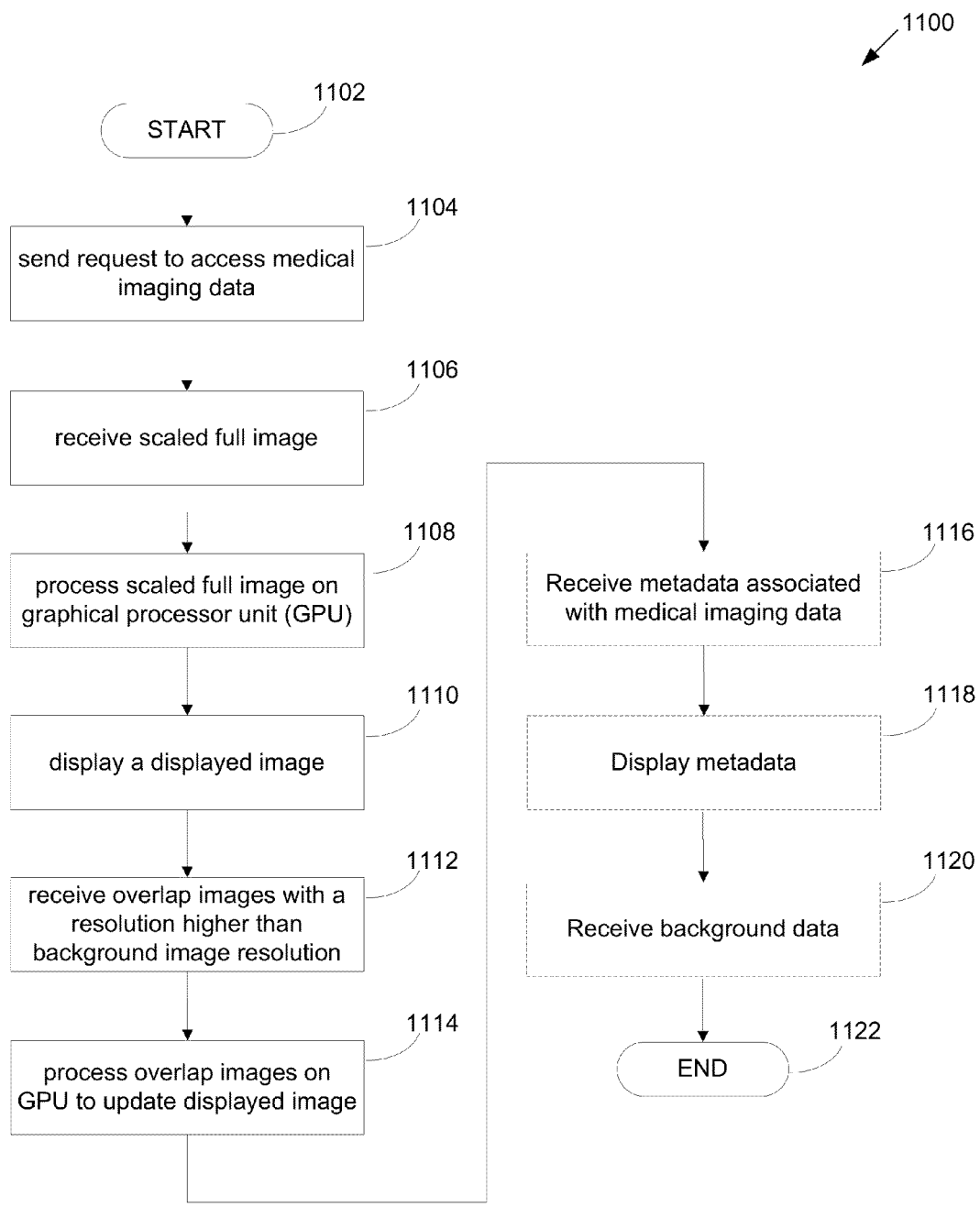
FIG. 11 is a flowchart for an exemplary method for displaying medical imaging data in accordance with one or more embodiments of systems and methods for image data management.

FIG. 11 is a flowchart for an exemplary method for displaying medical imaging data in accordance with one or more embodiments of systems and methods for image data management. Process 1100 begins at step 1102.

Processing continues to step 1104, where a request to access medical imaging data from a server is sent. The medical imaging data may comply with the Digital Imaging and Communications in Medicine (DICOM) file format definition.

Processing continues to step 1106, where an initial image is received. The initial image may be a scaled full image of the medical image data. In one or more embodiments, the initial image is limited in size based on a GPU limitation.

Processing continues to step 1108, where the initial image is processed on a GPU to generate a displayed image. In one or more embodiments, the initial image is processed to reduce a bit depth of the initial image before processing the initial image on the GPU.

Processing continues to step 1110, where the displayed image is displayed on a display device. The displayed image includes at least a portion of the initial image.

Processing continues to step 1112, where a plurality of overlap images are received from the server. A resolution of the overlap images is higher than the resolution of the initial image received. The overlap images may correspond to an image display window.

Processing continues to step 1114, where the plurality of overlap images are processed on the GPU to update the displayed image. In one or more embodiments, the plurality of overlap images is processed to reduce a bit depth of the overlap images before processing the overlap images on the GPU. The bit depth may be selectively reduced to retain a specific subset of information present in the overlap images. In one or more embodiments, the plurality of overlap images is processed in series on the GPU based on the limitations of the GPU. When the GPU processes an overlap image, it may use at least a portion of the overlap image to update at least a portion of the displayed image. Upscaling and/or downscaling operations may be performed to update the displayed images.

Processing continues to optional step 1116, where metadata associated with the displayed image is received. The metadata may include data that complies with the DICOM file format definition. In one or more embodiments, the metadata includes analysis, diagnosis and/or treatment information made by a medical professional.

Processing continues to optional step 1118, where the metadata is displayed on the display device.

Processing continues to optional step 1120, where background data is received. In one or more embodiments, the background data includes unsent image data selected from a plurality of high-resolution tiles and the plurality of reduced resolution tiles that make up the tiled representation of a dataset. Background data may be streamed when no active request for other data from the server is pending. The background data may be prioritized based on one or more factors, such as any measure of distance from the current image display window.

Processing continues to step 1122, where process 1100 terminates.

Figure 12:
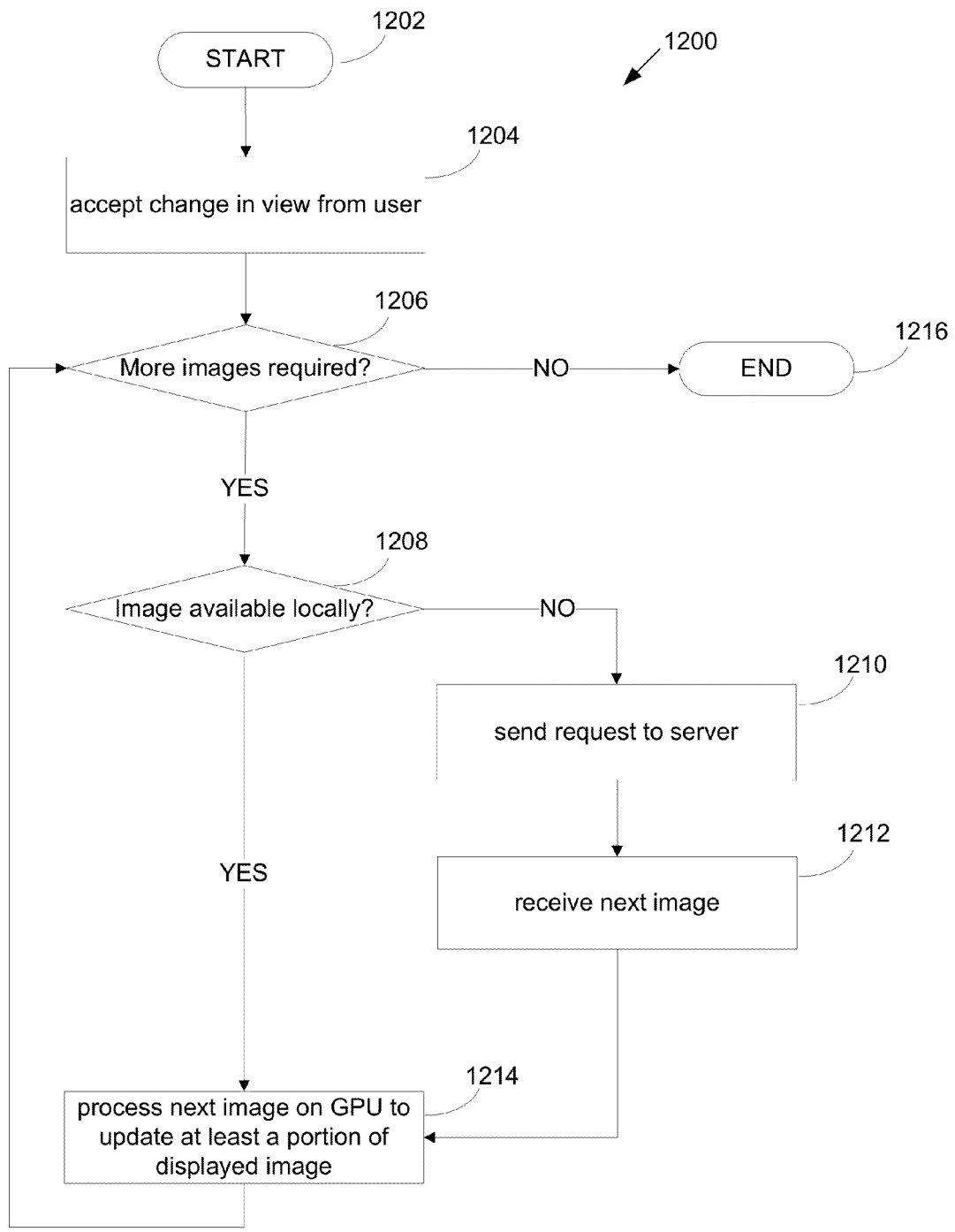
FIG. 12 is a flowchart for an exemplary method for image data collaboration in accordance with one or more embodiments of systems and methods for image data management.

FIG. 12 is a flowchart for an exemplary method for image data collaboration in accordance with one or more embodiments of systems and methods for image data management. Process 1200 begins at step 1202.

Processing continues to step 1204, where a change in view from the user is accepted. A change in the view from the user may include a change in position and/or a change in resolution.

Processing continues to decision step 1206, where it is determined whether more images are required. In one or more embodiments, more images may be required when an image display window changes, such as when a user navigates image data.

When more images are still required, processing continues to decision step 1208, where it is determined whether the images are available locally. An image may be available locally if it was stored after it is initially received in response to a request. An image may also be available locally if it was received as background data.

If images are available locally, processing continues to step 1214. If images are available not available locally, processing continues to step 1210, where a request is sent to a server for more image data. In one or more embodiments, the images required are determined locally. Such images may be defined based on at least one of position information and resolution information. Alternatively, the images required may be determined by the server.

Processing continues to step 1212, where the next requested image is received from the server. In one or more embodiments, all images required are requested in one step, and processing continues based on the availability of each image.

Processing continues to step 1214, where the next image is processed on the GPU to update at least a portion of the displayed image. In one or more embodiments, the plurality of overlap images is processed in series on the GPU based on the limitations of the GPU. When the GPU processes an overlap image, it may use at least a portion of the overlap image to update at least a portion of the displayed image. Upscaling and/or downscaling operations may be performed to update the displayed images.

Processing continues to decision step 1206.

Returning to decision step 1206, if no more images are required, processing continues to step 1216, where process 1200 terminates.

Figure 13:
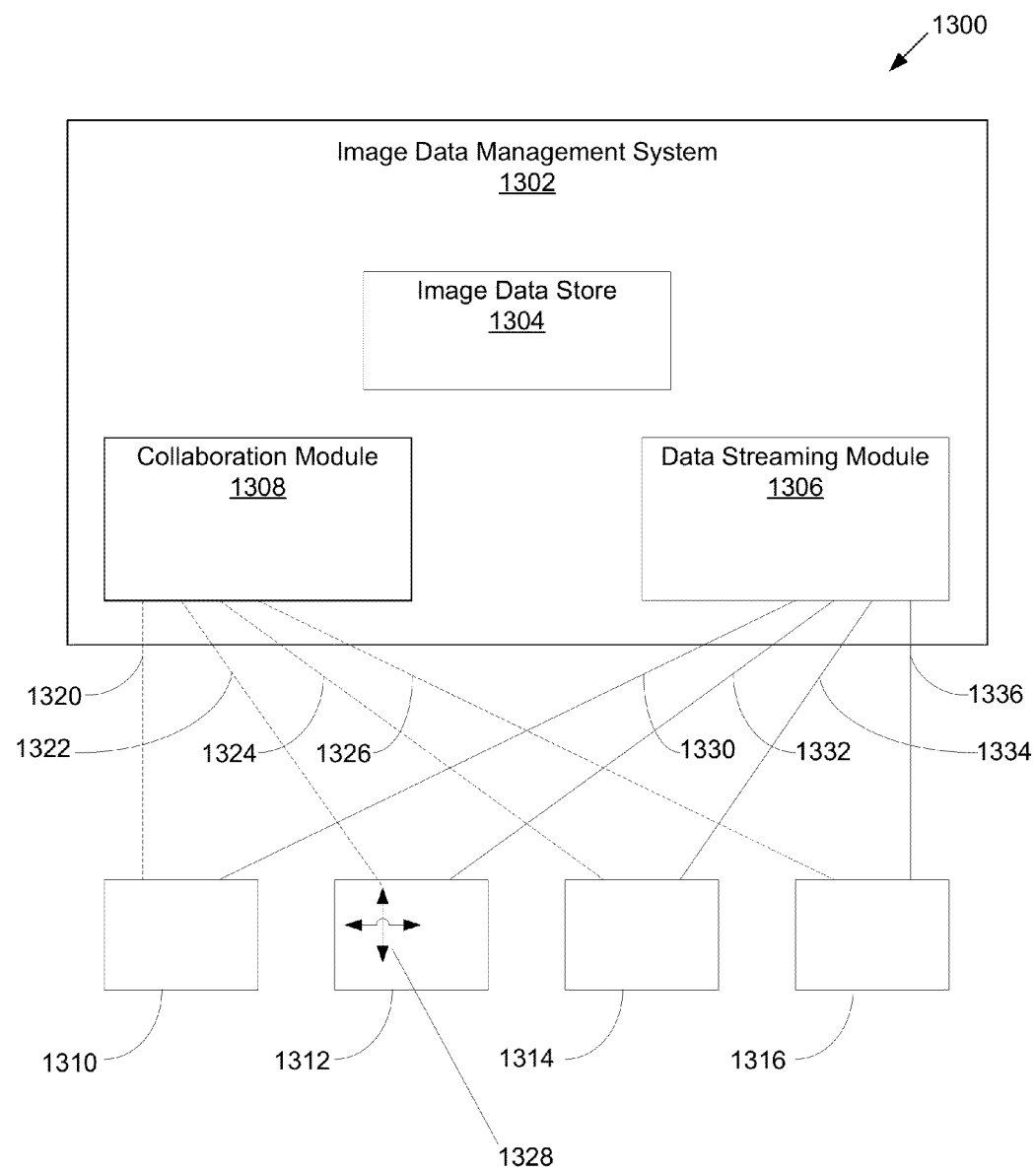
FIG. 13 illustrates an exemplary collaborative image data management system in accordance with one or more embodiments of systems and methods for image data management.

FIG. 13 illustrates an exemplary collaborative image data management system in accordance with one or more embodiments of systems and methods for image data management. System 1300 includes image data management system 1302 and client devices 1310-1316.

Image data management system 1302 includes collaboration module 1308.

Collaboration module 1308 is configured to manage one or more collaboration sessions between a plurality of client devices. In the example shown, collaboration module 1308 is managing a collaboration session between client devices 1310-1316.

Each client device 1310-1316 is connected to collaboration module 1308 over network connections 1320-1326. In one or more embodiments, network connections 1320-1326 are lightweight network connections capable of handling low bandwidth image navigation information. The image navigation information is generated by controlling client device 1312. Controlling client device 1312 possesses session navigation control key 1328. In one or more embodiments, any of client devices 1310-1316 may request session navigation control key 1328. Alternatively, session navigation control may be restricted to specific client devices. In one or more embodiments, network connections 1320-1326 are further capable of handling communication, including voice and text communication between client devices 1310-1316. In a higher-bandwidth application, network connections 1320-1326 may be enabled to handle video communication between client devices 1310-1316. Communication may be directed to all client devices in a collaboration session or any subset thereof. In the case that network connection 1322 of controlling client device 1312 is interrupted, session navigation control key 1328 may be passed to another client device 1310-1316.

Image data management system 1302 further includes image data store 1304 and data streaming module 1306. Data streaming module 1306 is configured to deliver at least a portion of a tiled representation stored in image data store 1304 and to client devices 1310-1316. The data provided by data streaming module 1306 is delivered over network connections 1330-1336. Each client device 1310-1316 maintains an independent network connection 1330-1336 to request and receive image data.

Client devices 1310-1316 are configured to request data from data streaming module 1306 based on image navigation data received from collaboration module 1308. Controlling client device 1312 may request data from data streaming module 1306 either based on navigation data generated by its user, or navigation data received from collaboration module 1308 to ensure synchronization of navigation between controlling client device 1312 and other client devices in the collaboration session.

Network connections 1320-1326 and 1330-1336 may include connections over one or more networks, including one or more Local Area Networks (LAN), Wide Area Networks (WAN), wireless networks, cellular data networks, optical networks, distributed networks, the Internet, or any combination thereof.

While the invention herein disclosed has been described by means of specific embodiments and applications thereof, numerous modifications and variations could be made thereto by those skilled in the art without departing from the scope of the invention set forth in the claims.

What is claimed is:

1. A method of accessing high resolution image data comprising:
   accessing a tiled representation of an image data at high-resolution, said tiled representation comprising a plurality of high-resolution tiles and a plurality of reduced-resolution tiles;
   receiving a request to access said image data from a computing device, wherein said computing device is communicatively coupled with a display device;
   determining an image display window based on said request from said computing device, wherein said image display window corresponds to a displayable area on said display device;
   determining at least one overlap image to send said computing device based on said image display window, wherein said at least one overlap image is selected from said plurality of high-resolution tiles and said plurality of reduced resolution tiles; and
   sending at least a portion of said at least one overlap image to said computing device for display in real time.

2. The method of claim 1, wherein each of said plurality of high resolution tiles is based on a maximum tile size that is dependent on a GPU limit.

3. The method of claim 2, wherein said maximum tile size is 1024 pixels by 1024 pixels.

4. The method of claim 1, wherein said image data comprises a plurality of pixels at 16 bits per pixel.

5. The method of claim 1, wherein said plurality of reduced resolution tiles comprise resolutions of ½" in each dimension compared to said high resolution tiles, where n is an integer greater than or equal to 1.

6. The method of claim 1, wherein said at least one overlap image comprises a plurality of tiles at a new resolution, wherein said new resolution is the next higher resolution generated compared to a resolution currently displayed on said display device.

7. The method of claim 1, further comprising:
   receiving a request from said computing device to access data corresponding to an updated image display window;
   determining at least one updated image to send said computing device based on said updated image display window, wherein said at least one updated image is selected from said plurality of high-resolution tiles and said plurality of reduced-resolution tiles; and
   sending said at least one updated image to said computing device for display in real time.

8. The method of claim 1, wherein said image data comprises full-resolution medical imaging data.

9. The method of claim 1, further comprising providing metadata associated with said image data to said computing device.

10. A method of accessing high resolution image data comprising:
    obtaining a high-resolution image data;
    generating a plurality of scaled full images from said high resolution image data at a plurality of resolutions comprising a full resolution image and at least one reduced resolution image;
    generating a plurality of high-resolution tiles based on said full resolution image;
    generating a plurality of reduced-resolution tiles based on said at least one reduced resolution image; and
    receiving a request to access said image data from a computing device, wherein said computing device is communicatively coupled with a display device;
    determining an image display window based on said request from said computing device, wherein said image display window corresponds to a displayable area on said display device;
    determining at least one overlap image to send said computing device based on said image display window, wherein said at least one overlap image is selected from said plurality of high-resolution tiles and said plurality of reduced resolution tiles; and
    sending at least a portion of said at least one overlap image to said computing device for display in real time.

11. The method of claim 10, wherein each of said plurality of high resolution tiles is based on a maximum tile size that is dependent on a GPU limit.

12. The method of claim 10, wherein said image data comprises a plurality of pixels at 16 bits per pixel.

13. The method of claim 10, wherein said plurality of reduced resolution tiles comprise resolutions of ½" in each dimension of said high resolution tiles, where n is an integer greater than or equal to 1.

14. The method of claim 10, wherein said image data comprises full-resolution medical imaging data.

15. The method of claim 14, wherein said medical imaging data complies with the Digital Imaging and Communications in Medicine (DICOM) file format definition.

16. A system for managing high resolution image data comprising:
    a server with high resolution image data;
    a computing device communicatively coupled to said server, wherein said computing device is configured with a display device and a graphical processor unit (GPU), wherein said computing device is further configured to:
    send a request to said server for a view said image data;
    receive an initial image from said server based on image display window of said display device, wherein said server determines said image display window from said request;
    display said initial image on said display device;
    receive a plurality of overlap images from said server, wherein a resolution of said plurality of overlap images is higher than a resolution of said initial image, and wherein said plurality of overlap images is limited in size;
    process said plurality of overlap images on said GPU to update at least a portion of said displayed image with at least a portion of said plurality of overlap images.

17. The system of claim 16, wherein said plurality of overlap images is limited in size based on limitation of said GPU.

18. The system of claim 16, wherein said image data comprises a plurality of pixels at 16 bits per pixel.

19. The system of claim 16, wherein said image data comprises full-resolution medical imaging data.

20. The system of claim 19, wherein said medical imaging data complies with the Digital Imaging and Communications in Medicine (DICOM) file format definition.

\* \* \* \* \*